(12) United States Patent
Schaupp et al.

(10) Patent No.: US 9,039,894 B2
(45) Date of Patent: May 26, 2015

(54) SUPPORTING PLATE OF A DEVICE

(75) Inventors: Bernd Schaupp, Seewald (DE);
Juergen Skott, Altensteig (DE);
Michael Braun, Altensteig (DE);
Soeren Groth, Herrenberg (DE);
Manfred Berndt, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 680 days.

(21) Appl. No.: 11/986,358

(22) Filed: Nov. 21, 2007

(65) Prior Publication Data

US 2010/0072122 A1 Mar. 25, 2010
US 2013/0256204 A9 Oct. 3, 2013

Related U.S. Application Data

(63) Continuation of application No. PCT/EP2005/052349, filed on May 23, 2005.

(51) Int. Cl.
*B01D 15/08* (2006.01)
*B01D 15/12* (2006.01)
(Continued)

(52) U.S. Cl.
CPC ...... *H05K 5/0004* (2013.01); *G01N 2030/3007* (2013.01); *G01N 2030/3015* (2013.01); *F04B 39/14* (2013.01); *B01D 15/12* (2013.01);
(Continued)

(58) Field of Classification Search
CPC ........ B01D 15/00; B01D 15/08; B01D 15/10; B01D 15/12; G01N 30/02; G01N 30/04; G01N 2030/00; G01N 2030/04; G01N 30/20; G01N 30/00; G01N 30/30; G01N 2030/027; G01N 2030/3007; G01N 2030/3015; F04B 23/00; F04B 39/12; F04B 39/14; F04B 53/22; F04B 39/00; B01L 9/00; B01L 9/06; B01L 9/52; B01L 2300/06
USPC ........... 73/61.52, 61.55; 210/198.2, 232, 656, 210/236; 248/346.03; 269/56, 287; 422/63, 422/69, 70, 99–104, 65, 500, 501, 509, 521, 422/522, 527, 534, 560–563, 565, 566; 436/161, 174, 43, 46–48, 180
See application file for complete search history.

(56) References Cited

U.S. PATENT DOCUMENTS 2,604,248 A * 7/1952 Gorham ...................... 141/130
2,967,633 A * 1/1961 Stegemann et al. ...... 414/416.03
(Continued)

FOREIGN PATENT DOCUMENTS

DE 196 12 167 A1 10/1997
EP 0 546 211 A 6/1993
(Continued)

OTHER PUBLICATIONS

Patent Abstracts of Japan, JP 2001 242149 A Sep. 7, 2001 Schmadzu Corp. Written Opinion of the international searching authority dated Feb. 9, 2006 International search report dated Feb. 9, 2006.

*Primary Examiner* — Joseph Drodge

(57) ABSTRACT

A supporting plate of a device is suggested. The device has at least one component and a housing for at least partly protecting the component. The supporting plate has at least one receiving element adapted for accepting the at least one component of the device in at least one of the following manners: in a form-closed manner, in a force-closed manner. The supporting plate is part of the housing.

10 Claims, 9 Drawing Sheets

(51) Int. Cl.
    *G01N 30/04*     (2006.01)
    *G01N 30/20*     (2006.01)
    *G01N 30/30*     (2006.01)
    *F04B 39/14*     (2006.01)
    *F04B 53/22*     (2006.01)
    *H05K 5/00*     (2006.01)
    *B01D 15/10*     (2006.01)
    *G06F 1/18*     (2006.01)
    *G01N 30/60*     (2006.01)

(52) U.S. Cl.
    CPC ................ *B01D15/10* (2013.01); *F04B 53/22* (2013.01); *G01N 30/04* (2013.01); *B01D 15/08* (2013.01); *G01N 30/30* (2013.01); *B01L 2300/06* (2013.01); *G01N 30/20* (2013.01); *G01N 30/6047* (2013.01); *G06F 1/183* (2013.01)

(56) References Cited

U.S. PATENT DOCUMENTS

| | | | |
|---|---|---|---|
| 3,477,478 A * | 11/1969 | Robertson et al. | 141/284 |
| 4,296,454 A | 10/1981 | Wong et al. | |
| 4,582,204 A * | 4/1986 | Wright | 211/133.1 |
| 4,926,291 A | 5/1990 | Sarraf et al. | |
| 5,207,918 A * | 5/1993 | Sanford et al. | 210/656 |
| 5,228,988 A * | 7/1993 | Sanford et al. | 210/198.2 |
| 5,273,718 A * | 12/1993 | Skold et al. | 422/553 |
| 5,441,645 A * | 8/1995 | Sanford et al. | 210/656 |
| 5,585,070 A * | 12/1996 | Lessard et al. | 422/535 |
| 6,197,198 B1 * | 3/2001 | Messinger et al. | 210/656 |
| 6,261,520 B1 * | 7/2001 | Kubacki et al. | 422/63 |
| 6,355,164 B1 * | 3/2002 | Wendell et al. | 210/198.2 |
| 6,436,351 B1 * | 8/2002 | Gubernator et al. | 422/553 |
| 6,562,232 B2 * | 5/2003 | Myogadani | 210/94 |
| 6,673,316 B1 * | 1/2004 | Okamoto et al. | 422/63 |
| 7,491,326 B2 * | 2/2009 | Schaefer | 210/198.2 |
| 2002/0116988 A1 * | 8/2002 | Davison et al. | 73/61.55 |
| 2005/0011835 A1 * | 1/2005 | Henderson et al. | 210/656 |
| 2006/0048846 A1 * | 3/2006 | Roenneburg et al. | 141/130 |
| 2007/0181505 A1 * | 8/2007 | DeMarco | 210/656 |

FOREIGN PATENT DOCUMENTS

| | | |
|---|---|---|
| EP | 0 743 814 A | 11/1996 |
| JP | 2001242149 A1 | 9/2001 |

\* cited by examiner

SUPPORTING PLATE OF A DEVICE

This application is the National Stage of International Application No. PCT/EP2005/052349, filed on 23 May 2005 which designated the United States of America, and which international application was published as WO Publication No. WO 2006/125469 which is incorporated by reference in its entirety.

BACKGROUND ART

The present invention relates to a chassis of a device.

Such devices, for example, computers or electronic instruments, can comprise a variety of different components, for example, printed circuit boards, storage disks, ventilators, loudspeakers, hydraulic components, optoelectronic components, etc., which are typically mounted to a chassis. The chassis has the purpose to hold the individual components, mechanically stable, at a fixed location. Besides this, known devices comprise a housing for protecting the components and for improving the optical appearance of the device. The component is mounted, mechanically stable, within the housing.

A chassis according to the prior art can comprise a framework having several partitions to which the components are mounted. Another chassis in the prior art can comprise a support unit which is made of expanded polypropylene (EPP). The single components are fixed at their locations by connections with the EPP. The EP 0 546 211 B2 (by the same applicant), for example, shows such a chassis.

DISCLOSURE OF THE INVENTION

It is an object of the invention to provide an improved chassis of a device. The object is solved by the independent claims. Preferred embodiments are shown by the dependent claims.

According to embodiments of the present invention, a supporting plate of a device is suggested. The device comprises at least one component, for example, a hydraulic, analytic, detecting, cooling and/or optoelectronic component and a housing for at least partly protecting, covering, and/or surrounding the device and/or the component within the device. The supporting plate comprises an external surface realizing a part of the external surface of said housing of the device. The external surface of the supporting plate can be designed rugged and resistant and consequently adapted for protecting, covering, and/or surrounding the components of the device mounted inside the device or better behind the surface. For accepting the component, the supporting plate comprises at least one receiving element or accepting element. The receiving element can receive the component in a form-closed and/or in a force-closed manner. No special fixing elements, for example, rivets, screws, and/or alike are needed for assembling the component with the supporting plate. Advantageously, the supporting plate is part of the housing of the device. By this, the supporting plate can combine two functions in one part: holding the component in place and housing the device. In other words, the supporting plate is a part of a chassis and of a housing of the device. This simplifies the design of the resulting device, reduces parts, and consequently permits a cost optimized assembly.

Other embodiments may include one or more of the following. The receiving element of the supporting plate can be adapted for receiving the component by simple hand-fitting. The component can be inserted into the receiving element manually. For this purpose the receiving element can comprise one or more margins, walls, recesses, detent mechanisms, or alike adapted to the outer shape of the component. Therefore no special tools are needed for assembling and/or maintaining the device. Advantageously, the supporting plate can comprise a plurality of receiving elements being adapted for receiving and fixing all components of the device.

Advantageously, the supporting plate can comprise a receiving element for receiving a second part of the housing of the device. The receiving element can be realized as a detent mechanism. For closing the housing, for example, after finishing assembly, the second part of the housing can simply be snapped into place.

Advantageously, the supporting plate can be L-shaped, wherein one part of the "L" can form a front cover of the device.

Embodiments may comprise one or more of the following. The supporting plate can comprise a composite material. Advantageously, the receiving element can comprise the composite material, for example rubber, silicone, and/or plastic. Advantageously, the composite material can be employed, for example, for vibration absorption, thermal insulation, shielding, fire control, and/or alike. No additional parts are needed for protecting sensitive parts. The supporting plate can be part of a shielding. For this purpose, the supporting plate can comprise a conductive coating. It can be, for example, metal-coated or metal-evaporated.

Embodiments may comprise one or more of the following. The supporting plate can be made out of one integral part, for example, by injection molding. Advantageously, the injection molding compound can be a thermoplastic material. The molding compound can be injected under relative low pressure into the mold and foamed, for example, between 6 to 8% of its original volume. For this purpose, the injection molding compound can comprise a gas developing agent. This results in a stiff closed-cell foam having a slight cellular structured core and a closed outer skin. Advantageously, this method enables thick-walled, large flat shaped, dimensionally stable, non-deforming, and stiff parts applicable without additional finish. Advantageously, nearly all known thermoplastic materials can be employed as basis material. Besides this, for example, steps of the wall thickness up to 40 mm can be realized without sink marks. If desired, the material can be fiber-reinforced, for example, glass-fiber reinforced and/or coated, for example, paint-coated or metal-coated.

Advantageously, the composite material can be installed easily during the molding process.

Embodiments may comprise one or more of the following. The supporting plate can be used for a device being part of a rack-system and/or for the rack itself. The rack is adapted for accommodating and supplying more than one device and comprises commonly used components, for example, the power supply for the devices. Therefore, the supporting plate can comprise a connector for connecting the rack with the device, wherein the connector is adapted for connecting the device automatically to the rack after inserting the device into the rack. For this purpose, the supporting plate can comprise a slide rail or better a pair of slide rails adapted for inserting and form-fitting the device into the rack. The rack can comprise according slide rails. Advantageously, the slide rail comprises a detent mechanism interacting with according parts of the rack, for example, an according notch, for catching the device in the rack. Advantageously, the detent mechanism of the slide rail can be detached manually and/or with simple tools. Especially advantageously, the slide rail can comprise the detent mechanism.

The housing of the device can be, in particular in combination with the rack, partly open. In other embodiments, the device and/or the housing of the device can comprise a foam. Foams for receiving components of devices are known in the art from EP 0 546 211 B2 (by the same applicant), which is, in particular the Figs. and the according description, incorporated herein by reference. The advantages of the stiff supporting plate can be combined with the advantages of the foam to an advantageous device, but with a simplified design. In further embodiments, the housing can comprise metal. Advantageously, the metal part can be combined with the supporting plate to realize a housing, in particular a complete housing.

Further embodiments of the invention relate to a device comprising at least one component and a supporting plate. Embodiments may comprise one or more of the following. Advantageously, the supporting plate comprises a stiff material and is part of a housing of the device. Advantageously, the supporting plate can fulfill two requirements in just one part: realizing a part of the housing and supporting the at least one component. The supporting plate is part of a chassis of the device. Advantageously, the at least one component can be held without fastening elements in a corresponding recess of the supporting plate of the device, respectively, due to a form-closed or force-closed connection of the components with the material of the supporting plate. Besides this, the supporting plate can be adapted for being combined with a cover element, for example, a foam.

The supporting plate can comprise a molded and slightly foamed thermoplastic material. Besides this, the device can be part of a liquid separation system for separating and/or analyzing a liquid, for example, a high performance liquid chromatography (HPLC) system, for example, installed into a rack. In other embodiments, the device can be a rack or a stack of various components realizing a liquid separation system, for example, a HPLC system. The device can be realized as a pump, for example, a binary pump or an isocratic pump, a thermostatted column compartment, an interface, an auto sampler, for example, a well-plate auto sampler or a micro-auto sampler, a detector, for example, a variable wavelength detector, a multi-wavelength detector, a diode-array detector, or a fluorescence detector, and/or a switching valve.

Other embodiments of the invention relate to a rack adapted for accommodating, connecting, and/or supplying at least one device and/or at least one supporting plate, in particular a device and/or a supporting plate. The rack and the devices can realize a liquid separation system, for example, a HPLC System.

Embodiments may comprise one or more of the following. The at least one supporting plate and the at least one device can be inserted into the rack. By this, the single devices can be combined to different systems. For maintaining the system, each of the devices can be removed separately.

The rack comprises at least one common component, for example a power supply and/or main board for supplying the at least one device. Advantageously, the devices installed into the rack can be designed for saving costs without said common components of the rack. Besides this, the rack can realize a housing for at least partly accommodating the at least one device. In other words, the at least one device can be designed with a cheaper interrupted housing. For connecting the at least one device easily after or while inserting it into the rack, the rack can comprise at least one connector.

For supporting the at least one common component, the rack can comprise a supporting plate comprising at least one receiving element adapted for receiving the component. Advantageously, the supporting plate and parts of the rack realize the housing of the device. Besides this, the rack can comprise a slide rail adapted for guiding the at least one device while inserting it into the rack and adapted for form-fitting fixing the at least one device. Advantageously, the rack and the at least one device can comprise a detent mechanism for fixing the device easily and automatically into the rack after inserting it. Advantageously, the slide rail can comprise the detent mechanism. The supporting plate of the at least one device can comprise an L-shaped portion, wherein the L-shaped portion and parts of the rack, for example, a top plate, a back wall, a supporting plate, and two side walls, realize a housing for at least partly surrounding the at least one device.

Finally, embodiments of the invention relate to a method of assembling a device. The device comprises a supporting plate out of a stiff material, for example, as described above. The device can be assembled manually simply by hand-fitting components to according receiving elements of the supporting plate. In embodiments, in a further step, the supporting plate can be assembled or better fitted with a cover-part for realizing a housing of the device. Advantageously, the supporting plate realizes a part of the housing. In embodiments, the device can be inserted into a rack, in particular after assembling and closing the housing.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 1 shows a three-dimensional exploded front side top view of a supporting plate 1 of a pumping device 3 of a HPLC system 5. The supporting plate 1 comprises receiving elements 7 for accepting components 9 of the pumping device 3.

Figure 1:
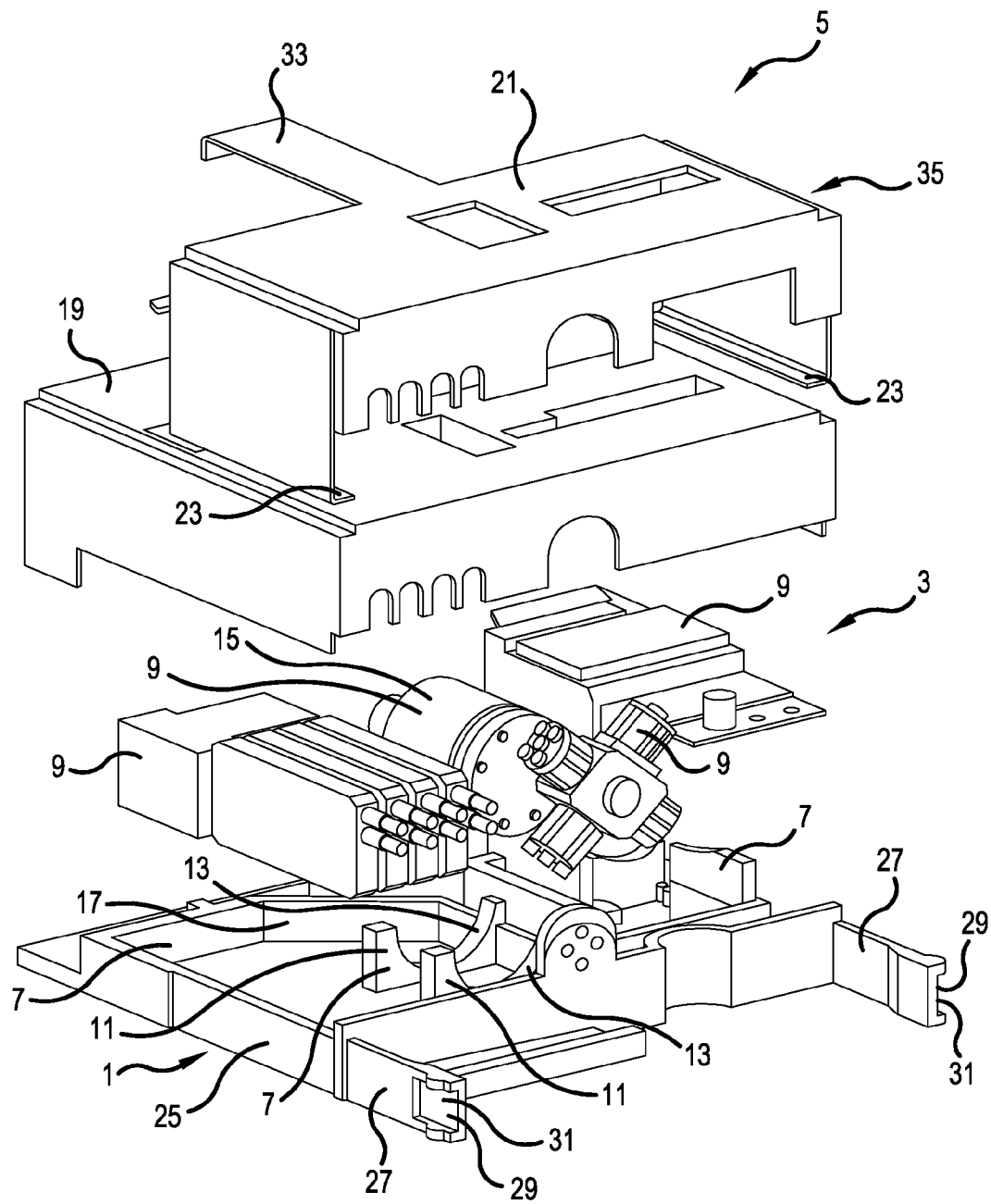
FIG. 1 shows a three-dimensional exploded front side top view of a pumping device of a HPLC system with a supporting plate comprising receiving elements for accepting components of the device.

The shapes of the receiving elements 7 of the pumping device 3 can be varied and consequently adapted to different outer shapes of the components 9 of the pumping device 3. For example, one of the receiving elements 7 is designed as a combination of two walls with walls 11 each having a circular recess 13. The recesses 13 of the walls 11 are adapted for accepting a cylindrically shaped component 15 of the pumping device 3 in a form-fitting and/or force-fitting manner. Other receiving elements 7, for example, are designed as walls 17 without recesses.

For covering the components 9 of the pumping device 3, the pumping device 3 can comprise an additional cover element 19. The cover element 19 can comprise a foam, for example, an expanded polypropylene (EPP) foam. The supporting plate 1 can be combined with the foam. Consequently, the foam and the supporting plate 1 can enclose the at least one component 9. The cover element 19 or better the foam can comprise a resilient plastic material and at least one recess in which fits the outer shape of the at least one component 9. In other words, the cover element 19 comprises also according—not visible—receiving elements. For assembling the pumping device 3, firstly all components 9 of the pumping device 3 can be fit, for example manually, to the receiving elements 7 of the supporting plate 1. In a second step, the cover element 19 or better the foam of the cover element 19 comprising the not visible receiving elements is put together with the supporting plate 1 comprising the components 9. The supporting plate 1 and the cover element 19 realize a chassis of the device 3.

Finally, the pumping device 3 can comprise an additional housing element, for example, a valance 21 for realizing a shielding for the components 9 inside the pumping device 3. For realizing a surrounding shielding, advantageously the supporting plate 3 can comprise a conductive coating, for example, a metal coating. The valance 21 can be adapted to the outer shape of the assembled cover element 19 and the supporting plate 1. For realizing a first detent mechanism 23, the valance 21 comprises 2 borders. As a final step, for assembling, the pumping device 3, the valance 21 or better the borders of the first detent mechanism 23 can be snapped in place with two according recesses 25 of the supporting plate 1 located at the sides of the supporting plate 1. The valance 21 can grasp the supporting plate 1. In embodiments, any other method of fixing two parts can be used instead of the first detent mechanism 23, for example, a simple belt, or alike.

The housing element or better the valance 21 and the supporting plate 1 provide a housing for the device, wherein the housing surrounds at least partly the device 1 and/or the components 9 of the device 1. Advantageously, the supporting plate 1 and the cover element 19 can realize a chassis of the device 1 being covered at least partly by the housing, namely by the supporting plate 1 and the housing element realized, for example, by the valance 21.

The recesses 25 of the supporting plate 1 are recessed into a left side and a right side slide rail 27. The slide rails 27 are adapted for inserting the completely assembled pumping device 3 into a not shown rack adapted for accommodating, supplying, and connecting the pumping device 3 within the rack. Advantageously, the supporting plate 1 or better the slide rails 27 of the supporting plate 1 comprise a second detent mechanism 29 for fixing the pumping device within the not shown rack. For sliding the pumping device 3 into the rack, the rack comprises an according slide rail. For fixing, for snapping the pumping device 3 in place, the rack can comprise an according protrusion or notch being adapted for engaging with the recess 31 of the second detent mechanisms 29. Besides this, the accepting element 7 of the supporting plate 1 can comprise and/or realize a third detent mechanism for fixing the component 9 of the device 3 with the supporting plate 1.

The valance 21 comprises a contact tag 33 for grounding the pumping device 3. The contact tag 33 can connect the valance 21 via an according contact of the rack to the ground.

Figure 2:
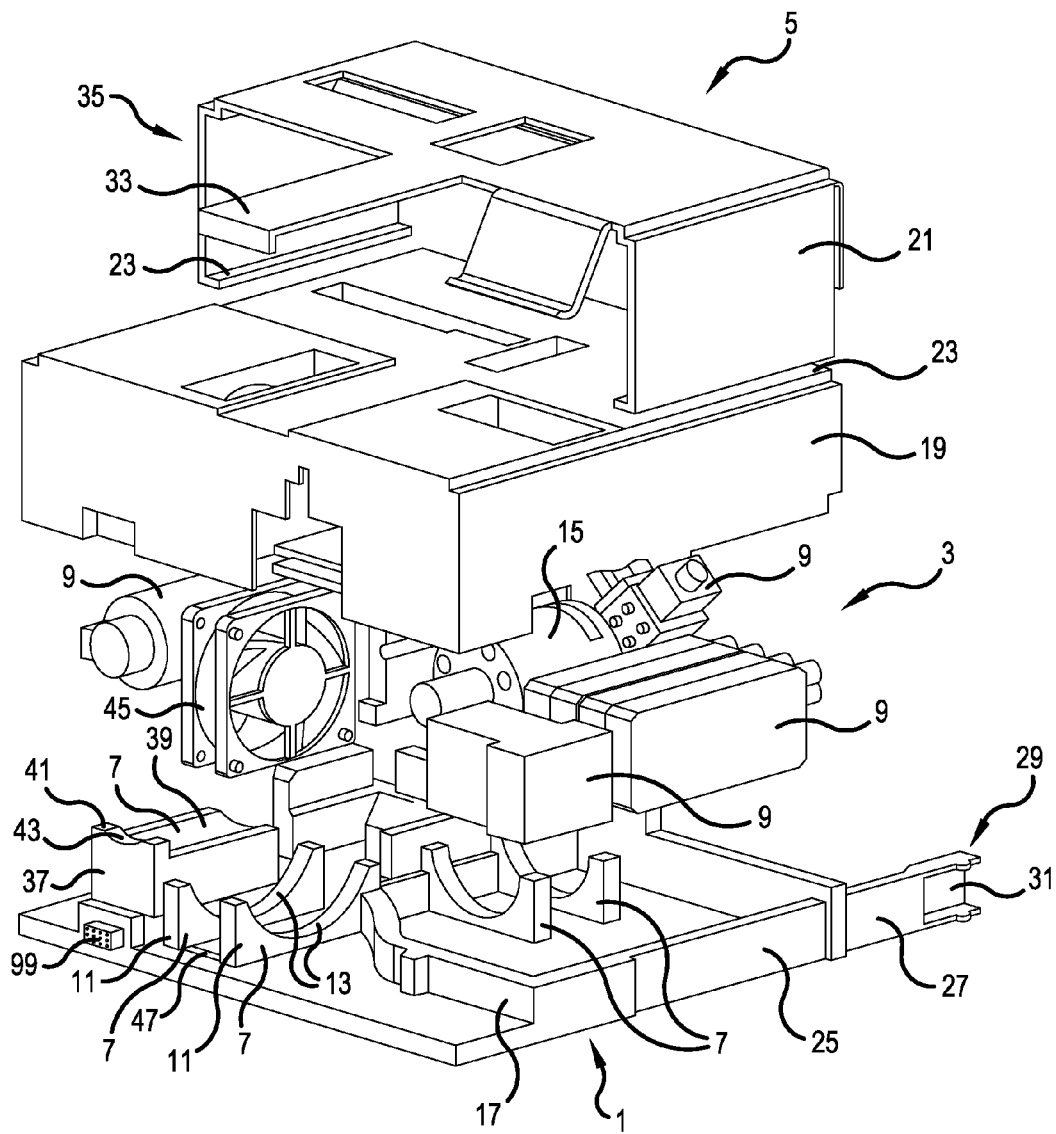
FIG. 2 shows the device of FIG. 2, but in a back side top view.

FIG. 2 shows the pumping device 3 of FIG. 1, but in a three-dimensional back side top view. When assembled, the supporting plate 1, the cover element 19 and the valance 21 together realize a housing 35 for protecting the components 9 of the pumping device 3. The housing 35 can be partly open, because of the fact that the pumping device 3 can be inserted into the not shown rack. For using the pumping device 3 as a stand alone device, the valance, for example, can be extended to a completely closed housing 35 in combination with the supporting plate 1. In other not shown embodiments, an additional not shown component part can be combined with the supporting plate 1 of the pumping device 3 to form a completely closed housing 35. In other embodiments, the pumping device 3 can simply comprise the supporting plate 1 and the components 9 fixed by the receiving elements 7 to the supporting plate 1. The housing 35 is then partly open and simply comprises the outer surface of the supporting plate 1.

In FIG. 2 another receiving element 7 of the supporting plate 1 of the pumping device 3 is visible. Said receiving element 7 is designed as a substantial rectangular solid or cubuid 37 comprising a partly cylindrical flute 39 and a margin 41, wherein the margin 41 comprises also a partly cylindrical flute 43 having a smaller diameter. The receiving element 7 comprising the cubuid 37 is adapted for accepting a cylindrically shaped component 9 comprising two different cylinders with different diameters.

Also visible in FIG. 2 is another component of the pumping device 3, a ventilator 45. According to the outer shape of the ventilator 45, the supporting plate 1 of the pumping device 3 comprises two more walls 11 with partly circularly shaped walls for accepting the ventilator 45. Additionally, for example, for realizing a vibration absorption, the receiving element 7 for accepting the ventilator 45 comprises a composite material 47.

The composite material 47 can comprise, for example, rubber, silicone, and/or elastic plastic material. The composite material 47 can be added to the supporting plate 1 in a second production or better molding step, for example, with a second injection mold, of the molding process for producing the supporting plate 1. Producing parts with component materials in molding processes is known in the art and therefore not described in detail in this application. In other embodiments, the second material can be applied by gluing, heat-sealing, fritting, or alike.

Figure 3:
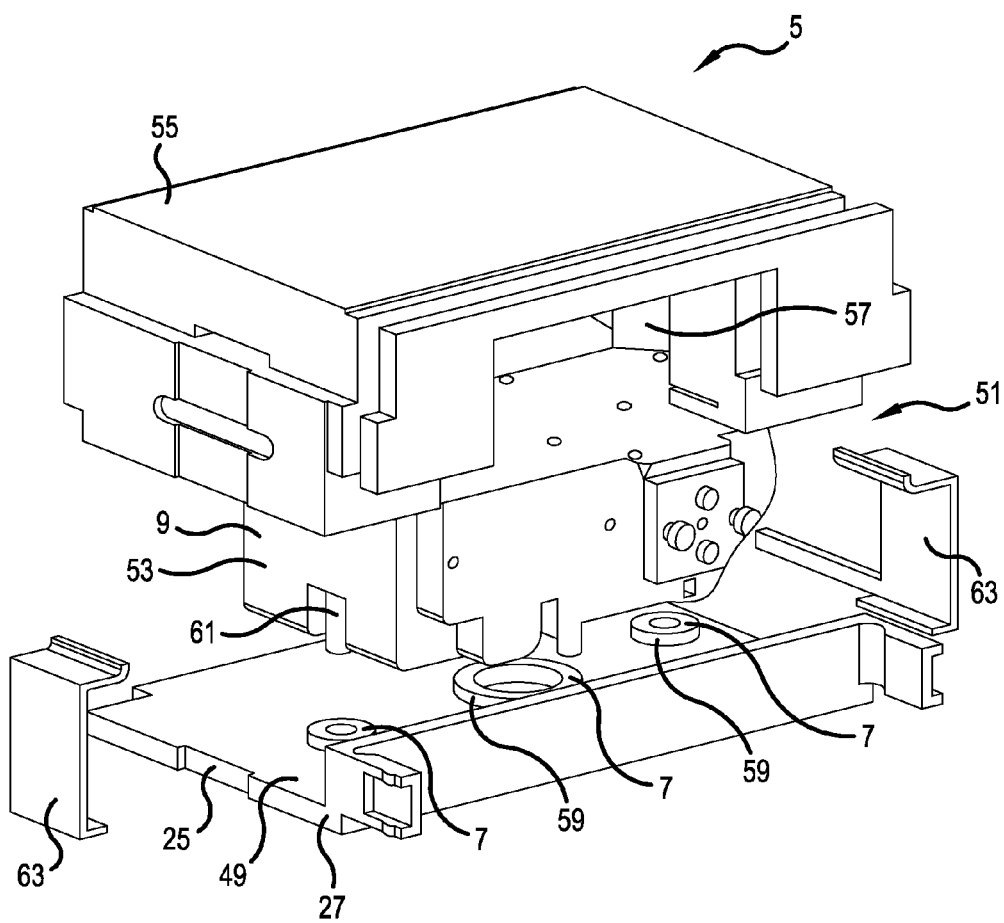
FIG. 3 shows a three-dimensional exploded front side top view of a detecting device of the HPLC system.

FIG. 3 shows a three-dimensional exploded front side top view of a supporting plate 49 for a detecting device 51 of the HPLC system 5. The detecting device 51 comprises a detector 53 adapted for detecting components within a liquid. The detecting device comprises a cover element 55, for example a cover element comprising a foam, for example, an EPP foam. The cover element 55 comprises a recess 57 for receiving the detector 53 in a form-fitting and/or force-fitting manner.

The supporting plate 49 comprises receiving elements 7 realized as cylindrically shaped walls 59. The detector 53 comprises pins 61. The pins 61 can be inserted or engaged into the internal circles of the circularly shaped walls 59 of the receiving elements 7 of the supporting plate 1 of the detecting device 51 for holding the detector 53 in place in a form-fitting and/or force-fitting manner. Therefore, the pins 61 being engaged into the inner circles of the circularly shaped walls 59 can realize a press fit. For assembling the detecting device 51, the detector 53 can simply be pushed manually downwards the circular walls 59 of the receiving elements 7. In a second step, the cover element 55 with the recess 57 can be put on the mounted detector 53. For holding the cover element 55, the detecting device can comprise clamps 63. The clamps 63 can be recessed into the recesses 25 of the slide rails 27 of the supporting plate 49.

The FIGS. 4 to 7 show three-dimensional front side top views of a rack 65 adapted for accommodating, connecting, and/or supplying, for example, the devices 3 and 51.

Figure 4:
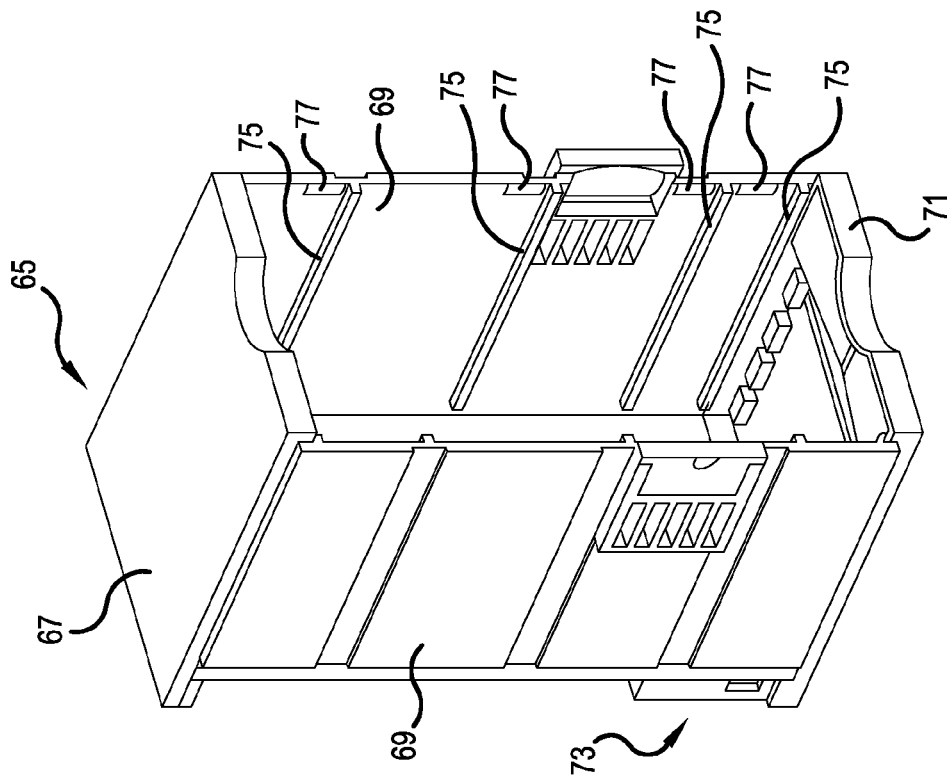
FIG. 4 shows a three-dimensional front side top view of a partly assembled rack for accommodating, connecting, and supplying devices.
Figure 5:
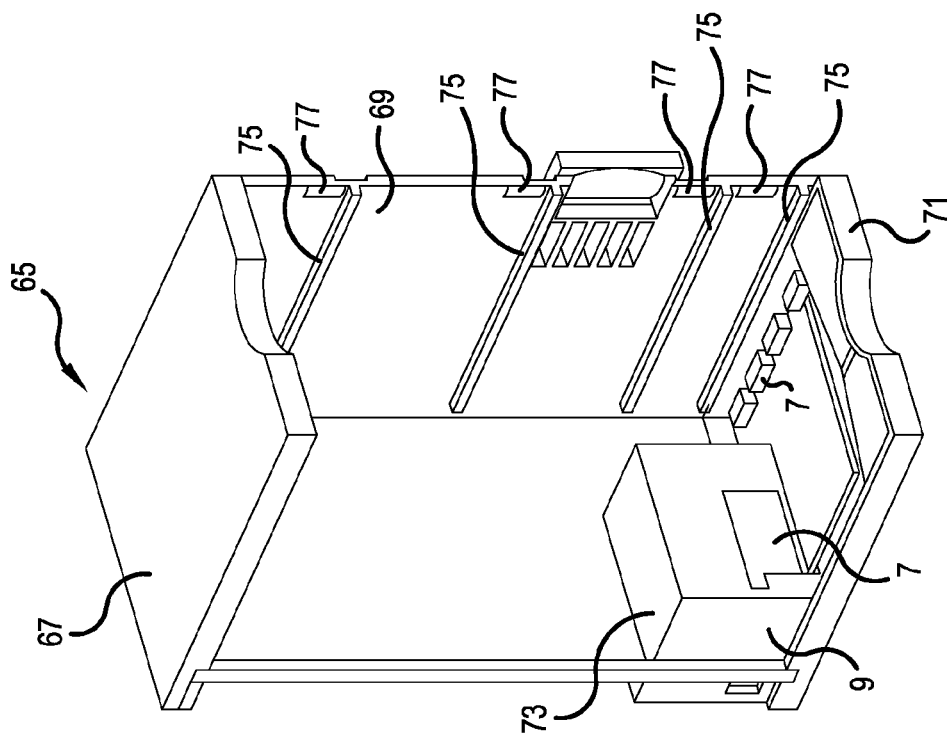
FIG. 5 shows the rack of FIG. 4, but completely assembled.

FIG. 4 shows the rack 65 in a partly and FIG. 5 in a completely assembled stage. The rack 65 comprises housing elements, for example, a top plate 67, two side walls 69, and one supporting plate 71. The supporting plate 71 of the rack 65 comprises also receiving elements 7 for accepting components 9 of the rack 65. The rack 65 comprises commonly used electronic components, for example, a common power supply 73 and/or a not shown main board. Principally, the supporting plate 71 of the rack 65 can comprise the same design and material as the supporting plates 1 and 49 of the devices 3 and 51 as described with the FIGS. 1 to 3.

FIG. 4 shows the rack 65 in a partly assembled stage, wherein the power supply 73 is visible. The side walls 69 of the rack 65 each comprise four slide rails 75 for interacting with the slide rails 27 of the devices 1 and 49. Besides this, each of the side walls 69 comprises four notches 77 adapted for interacting with the recesses 31 of the second detent mechanisms 29 of the devices 1 and 49. For mounting the side walls 69 of the rack 65, the side walls 69 comprise margins 79 as visible in a detailed view as shown in FIG. 11.

Figure 11:
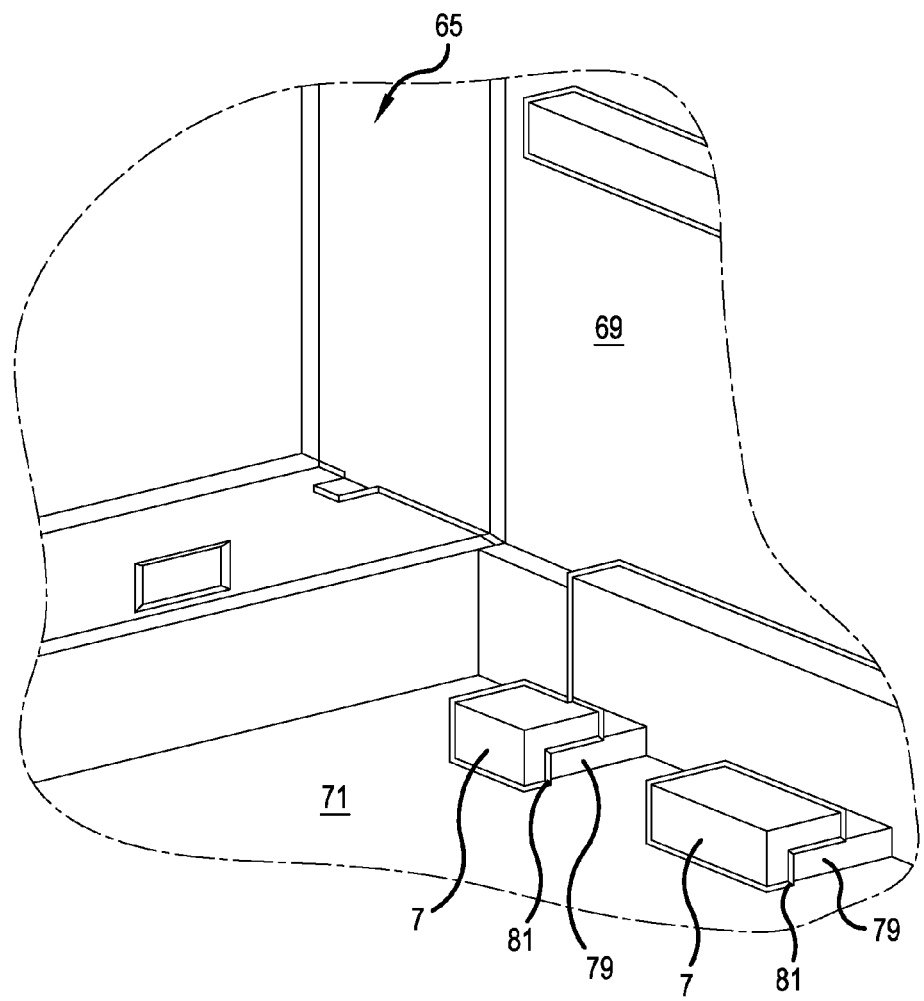
FIG. 11 shows a three-dimensional inner view of a detail of the supporting plate of the rack of the FIGS. 4 to 7 showing a detent mechanism for a side wall of the rack, and FIG. 12 exemplarily shows a schematic cross sectional view of a device having a supporting plate with a front cover.

FIG. 11 shows a part of the side wall 69 of the rack 65 in an assembled stage. The supporting plate 79 or better the receiving elements 7 of the supporting plate 71 form recesses 81 adapted for receiving the margins 79 of the side wall 69 in a form-fitting and/or force-fitting manner. For forming the recesses 81, the receiving elements 7 of the supporting plate 71 of the rack 65 are L-shaped.

Figure 6:
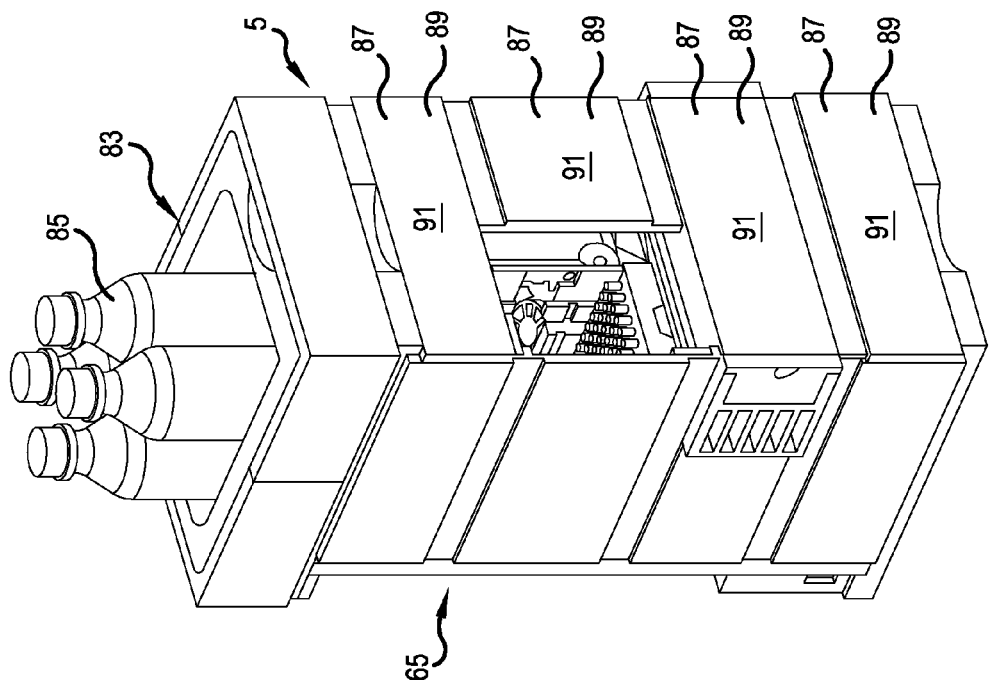
FIG. 6 shows the rack of FIG. 4, but completely equipped with devices of the HPLC system, wherein the devices comprise front covers.

FIG. 6 shows the rack 65 in combination with a solvent cabinet 83 adapted for storing different solvent bottles 85 needed for the HPLC system 5. The solvent cabinet 83 can simply be put onto the top plate 67 of the rack 65. In embodiments, the top plate 67 of the rack 65 and the solvent cabinet 83 can comprise a detent mechanism for simply snapping the solvent cabinet in place. In other embodiments, the solvent cabinet can be realized as a device adapted for sliding into the rack 65. Besides this, the rack 65 as shown in FIG. 6 is supported with four devices 87 being slit into the rack 65. The devices 87 are snapped in place and connected to the common components of the rack 65.

The devices 87 of the rack 65 comprise supporting plates 89 comprising each a front cover 91. The housing elements of the rack and the front covers 91 realize a housing for at least partly surrounding the devices 87 inserted into the rack 65.

Figure 12:
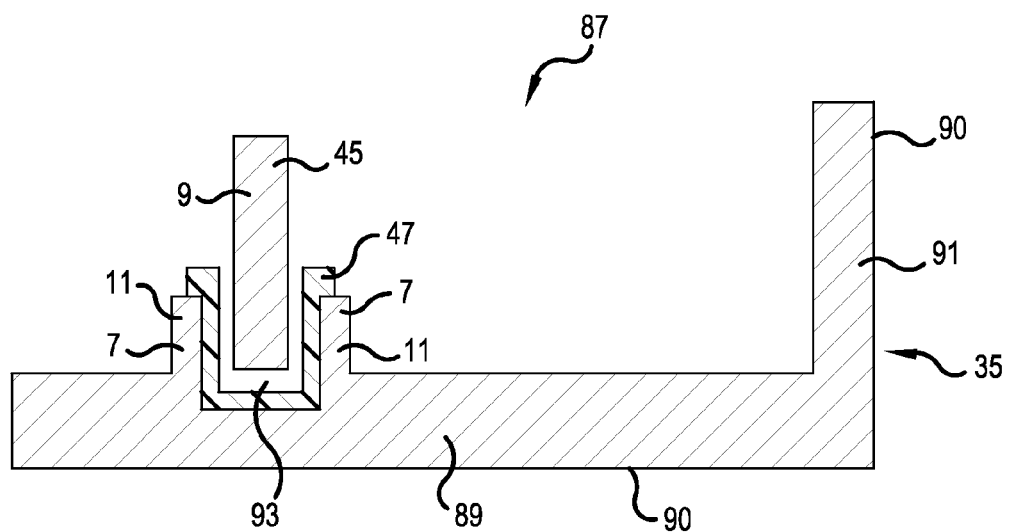

FIG. 12 exemplarily shows a schematic cross sectional view of a device 87 of the rack 65 with a supporting plate 89 and a front cover 91. The supporting plate 89 of the device 87 is L-shaped, wherein the vertical section of the "L" realizes the front cover 91 of the device 87. The front cover can improve the optical appearance of the device 87 and consequently of the completely assembled rack 65. Advantageously, the front covers 91 and the housing elements of the rack together provide a housing for the devices 87, wherein the single devices 87 don't need a complete housing.

The device 87 as shown in FIG. 12 exemplarily comprises one component 9, namely a ventilator 45. For absorbing the vibrations produced by the ventilator 45, the supporting plate 89 of the device 87 comprises a composite material 47. The composite material 47 can comprise an absorbing material, for example rubber, and/or an elastic artificial plastic material. The ventilator 45 can be inserted into the receiving element 7 of the supporting plate 89, for example, by press-fitting it into a recess 93 of the receiving element 7. The recess 93 of the receiving element 7 is realized by two parallel walls 11. Besides this, the supporting plate 89 comprises an external surface 90 realizing a part of the external surface of a housing 35 of the device 87. The external surface 90 of the supporting plate 87 can be designed rugged and resistant and consequently adapted for protecting, covering, and/or surrounding the components 45 of the device 87 mounted inside the device 87, in other words behind the surface 90.

Figure 7:
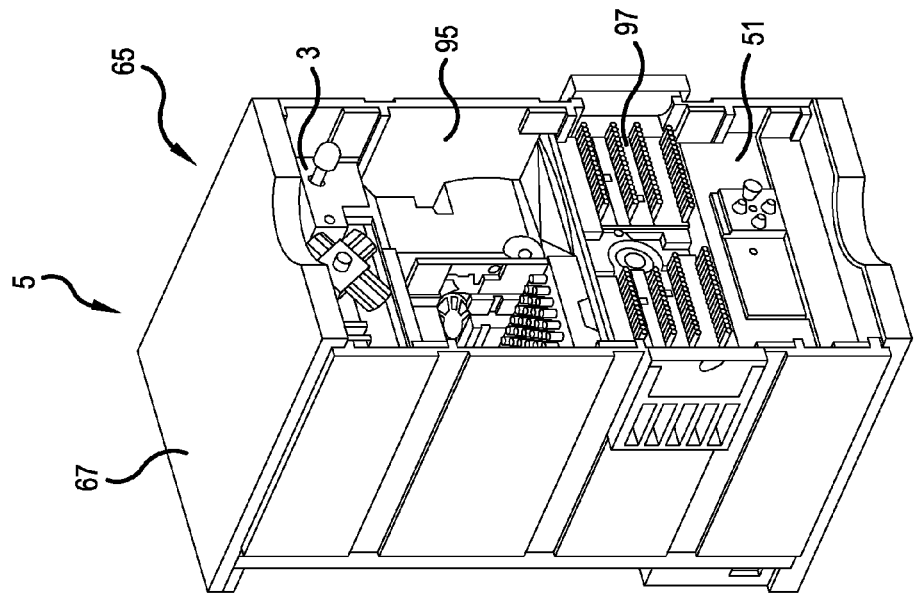
FIG. 7 shows the rack of FIG. 4, but completely equipped with devices without front covers.

The rack 65 as shown in FIG. 7 comprises devices without a front cover, for example, the pumping device 3 combined with a degasser as shown in the FIGS. 1 and 2, the detecting device 51 as shown in FIG. 3, an auto sampler device 95, and a thermostatted column device 97. The devices 3, 51, 95, and 97 realize the HPLC system 5 together with the rack 65. All the devices 3, 51, 95, and 97 are accommodated and supplied by the rack 65.

Figure 8:
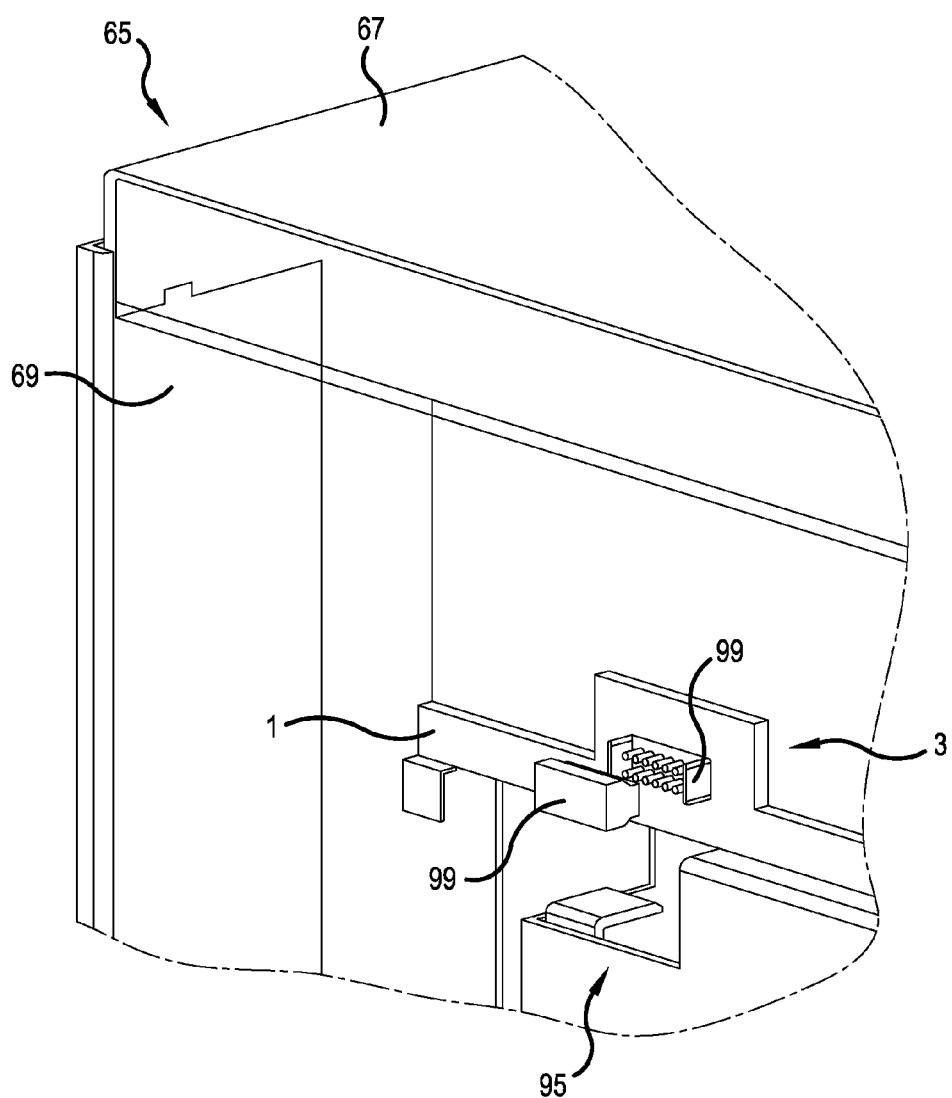
FIG. 8 shows a schematic three-dimensional front side top view of a detail of the rack of the FIGS. 4 to 7 showing a connector of a supporting plate of the device of the FIGS. 1 and 2.

FIG. 8 shows a detailed back top view of the rack 65 with the pumping device 3 showing a connector 99 adapted for connecting the pumping device 3 to the rack 65. The connector 99 is installed directly on the supporting plate 1 of the pumping device 3. The connector 99 can be closed simply and automatically by sliding the pumping device 3 into the rack 65.

Figure 9:
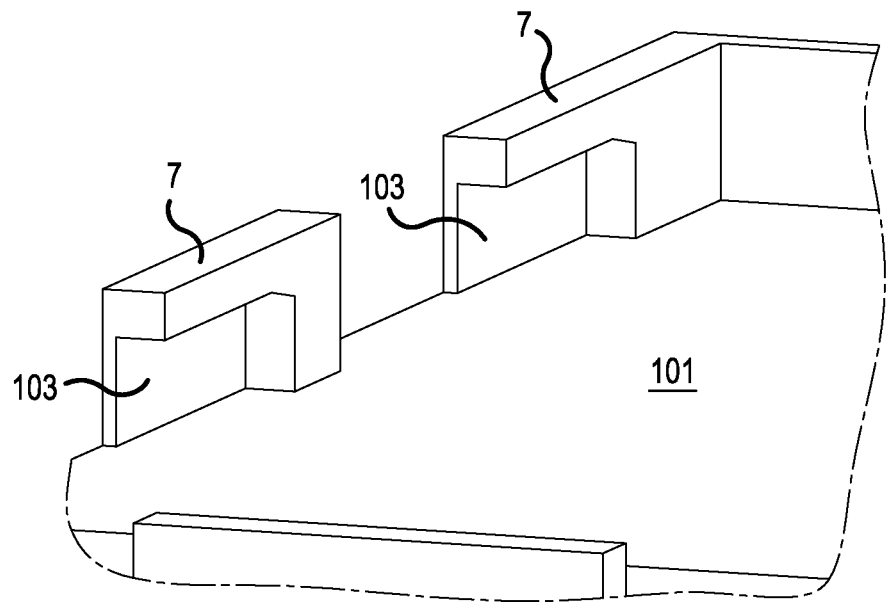
FIG. 9 shows a schematic three-dimensional front side top view of a detail of a supporting plate of the rack of the FIGS. 4 to 7.

FIG. 9 shows an exemplary three-dimensional detailed top front side view of a part of another base plate 101 with receiving elements 7. The receiving elements 7 of the base plate 101 comprise recesses 103. According margins of a not shown component can simply be slit in a form-fitting and/or force-fitting manner into the recesses 103 of the receiving element 7 of the base plate 101. The receiving elements 7 can hold the not shown component in place.

Figure 10:
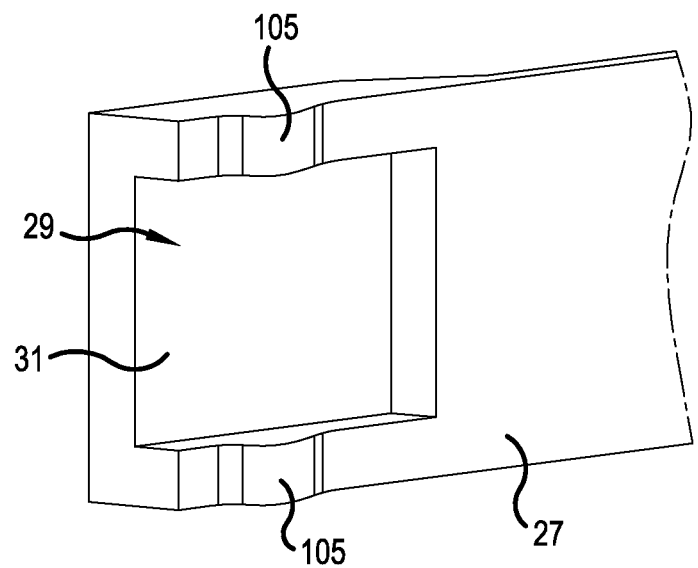
FIG. 10 shows a three-dimensional front side top view of a detail of a slide rail of a supporting plate showing a detent mechanism for the device into the rack.

FIG. 10 shows a detailed three-dimensional view of the side rail 27 of the supporting plate 1 of the pumping device as shown in the FIGS. 1 and 2. Visible is the recess 31 of the second detent mechanism 29 of the supporting plate 1. Besides this, the second detent mechanism 29 comprises two notches 105 adapted for engaging with according—not shown—recesses of the rack 65. The notches 105 can improve the holding power of the second detent mechanism 29. Besides this, the recess 31 of the second detent mechanism 29 can be dimensioned deeper than necessary for receiving the according notches 77 of the rack 65. This makes it possible to loosen the second detent mechanism 29 with a simple tool, for example, a screw driver. The screw driver can simply be inserted into the gap between the recess 31 and the according notch 77 of the side wall 69 of the rack 65.

It is to be understood, that this invention is not limited to the particular component parts of the devices described or to process steps of the methods described as such devices and methods may vary. It is also to be understood, that different features as described in different embodiments, for example illustrated with different Fig., may be combined to new embodiments. It is finally to be understood, that the terminology used herein is for the purposes of describing particular embodiments only and it is not intended to be limiting. It must be noted, that as used in the specification and the appended claims, the singular forms of "a", "an", and "the" include plural referents until the context clearly dictates otherwise. Thus, for example, the reference to "a device" or "a receiving element" includes two or more such functional elements.

The invention claimed is:

1. A liquid separation system, for at least one of separating and analyzing a liquid, comprising:
   a device comprising a chromatographic system;
   a rack system comprising at least one rack, the chromatographic system inserted into or being at least partly accommodated by the rack;
   a pumping device; and
   a supporting plate comprising receiving elements adapted and shaped to receive components of the pumping device, the supporting plate further comprising components configured to fix the pumping device within, or to be slidable into, and engage the rack system.

2. The liquid separation system of claim 1, the supporting plate further comprising
   a slide rail adapted for inserting and form-fitting fixing the device into a rack adapted for accommodating the device, wherein the supporting plate is part of a housing which at least partly houses the device, and wherein each of the receiving elements is configured to receive at least one component of the device in at least one of a form-closed and a force-closed manner.

3. The liquid separation system of claim 1, wherein at least one device is configured for performing a technical function, the liquid separation system further comprising:
   a housing which at least partly houses at least one device, wherein the supporting plate is part of the housing which at least partly houses the at least one device.

4. The liquid separation system of claim 3, wherein the rack system comprises at least one of:
   at least one component for supplying the at least one device;
   a housing for at least partly accommodating at least one of: the at least one device, the at least one common component, and the at least one supporting plate;
   at least one connector for connecting the at least one device.

5. The liquid separation system of claim 3, wherein the rack system comprises at least one of:
   at least one slide rail configured for guiding the supporting plate into the rack;
   two side walls each comprising one slide rail, wherein the slide rails of the rack are configured for interacting with the slide rails of the supporting plate.

6. The liquid separation system of claim 3, wherein the rack system comprises at least one of:
   the supporting plate is part of a chassis of the device;
   the supporting plate comprises an external surface, wherein the external surface is part of the housing of the device configured for at least one of: for protecting, covering, and surrounding components of the device;
   at least one of the supporting plate and the receiving element has at least one recess in which fits an outer shape of at least one of the components.

7. The liquid separation system of claim 3, wherein the rack system comprises at least one of:
   a first detent mechanism for fixing component parts of the housing of the device to the supporting plate;
   a second detent mechanism for fixing the device into the rack;
   a third detent mechanism for fixing the component of the device to the supporting plate;
   the slide rail comprises the second detent mechanism.

8. The liquid separation system of claim 3, wherein the rack system comprises at least one of:
   an L-shaped portion for forming a front cover of the device;
   a composite material comprising at least one of: rubber, silicone, plastic, wherein the composite material is used for realizing at least one of the following features: vibration absorption, thermal insulation, shielding, fire control, wherein the receiving element comprises the composite material;
   the supporting plate is part of a shielding;
   a stiff-molded and slightly foamed thermoplastic material;
   a connector for connecting the device to the rack;
   at least one of paint coating, conductive coating, metal coating.

9. The liquid separation system of claim 8, wherein:
   the device comprises a component part of a liquid separation system, comprising at least one of: a solvent cabinet, a micro vacuum degasser, a HPLC pump, an auto sampler, a temperature controlled column compartment, a detector; or
   the device comprises an electronic device comprising at least one of: a printed circuit board, a storage disk, and a ventilator; or
   the device comprises at least one of: a pump, a binary pump, an isocratic pump, a thermostatted column compartment, an interface, an auto sampler, a well-plate auto sampler, a micro-auto sampler, a detector, a variable wavelength detector, a multi-wavelength detector, a diode-array detector, a fluorescence detector, and a switching valve.

10. The liquid separation system of claim 8, wherein the rack system comprises at least one of:
   a foam for enclosing the at least one component together with the supporting plate, wherein the foam comprises a resilient plastic material;
   the supporting plate is configured for being combined with the foam and with an additional housing element which at least partly surrounds and protects the at least one component;
   the supporting plate together with the housing element provide at least one of the housing for and the chassis of the device.

* * * * *